US009149184B2

(12) United States Patent
Campbell

(10) Patent No.: US 9,149,184 B2
(45) Date of Patent: Oct. 6, 2015

(54) METHOD AND SYSTEM FOR IMAGING AMYLOID BETA IN THE RETINA OF THE EYE IN ASSOCIATION WITH ALZHEIMER'S DISEASE

(76) Inventor: Melanie Crombie Williams Campbell, Waterloo (CA)

(*) Notice: Subject to any disclaimer, the term of this patent is extended or adjusted under 35 U.S.C. 154(b) by 546 days.

(21) Appl. No.: 13/696,238

(22) PCT Filed: May 5, 2011

(86) PCT No.: PCT/CA2011/050275
§ 371 (c)(1),
(2), (4) Date: Feb. 22, 2013

(87) PCT Pub. No.: WO2011/137538
PCT Pub. Date: Nov. 10, 2011

(65) Prior Publication Data
US 2013/0208245 A1    Aug. 15, 2013

Related U.S. Application Data

(60) Provisional application No. 61/282,999, filed on May 5, 2010.

(51) Int. Cl.
*A61B 3/14* (2006.01)
*A61B 3/00* (2006.01)
*A61B 5/00* (2006.01)
*A61B 6/03* (2006.01)
A61B 6/00 (2006.01)

(52) U.S. Cl.
CPC ............... *A61B 3/14* (2013.01); *A61B 3/0025* (2013.01); *A61B 5/4088* (2013.01); *A61B 6/037* (2013.01); A61B 5/7264 (2013.01); A61B 6/506 (2013.01)

(58) Field of Classification Search
None
See application file for complete search history.

(56) References Cited

U.S. PATENT DOCUMENTS

2004/0152068 A1   8/2004  Goldstein
2009/0041666 A1*  2/2009  Goldstein et al. .............. 424/9.1
2011/0234977 A1*  9/2011  Verdooner ..................... 351/207
2011/0286932 A1* 11/2011  Koronyo et al. ............... 424/9.6

OTHER PUBLICATIONS

Koronyo-Hamaoui et al., Identification of Amyloid Plaques in Retinas From Alzheimer's Patients and Noninvasive In Vivo Optical Imaging of Retinal Plaques in a Mouse Model, NeuroImage, Jun. 13, 2010, pp. 5204-5217, 54, Elsevier Inc., http://www.elsevier.com/.

* cited by examiner

*Primary Examiner* — Long V Le
*Assistant Examiner* — Bradley Impink
(74) *Attorney, Agent, or Firm* — Lynn C. Schumacher; Hill & Schumacher

(57) ABSTRACT

The present invention describes methods to image amyloid beta in the retina of the eye in such a way as to diagnose and potentially treat Alzheimer's disease. The preferred apparatus to perform the image and treatment is described. The basic idea is to use an imaging method to characterize the depth location of amyloid beta (hereafter referred to as Aβ) in the retina, to classify and characterize the type of deposit, to quantify the amount present and thereby to diagnose Alzheimer's disease and stage the disease. The methods describe herein include image guided treatment of Aβ deposits in the retina.

56 Claims, 6 Drawing Sheets

Donut Shape: 6μm x 6μm to 8μm x 8μm
Height: ~1μm to 1.2μm

Fibular Shape: 20μm x 5μm to 95μm x 14μm
Height: ~ 0.5mμ to 1.5mμ

Globular Shape: 4μm x 7μm to 25μm x 20μm
Height: ~ 0.3 to 3.5

1          2          3

METHOD AND SYSTEM FOR IMAGING AMYLOID BETA IN THE RETINA OF THE EYE IN ASSOCIATION WITH ALZHEIMER'S DISEASE

CROSS-REFERENCE TO RELATED PATENT APPLICATIONS

This patent application is a National Phase application claiming the benefit of PCT/CA2011/050275 filed on May 5, 2011 in English, which further claims the priority benefit from, U.S. Provisional Patent Application 61/282,999 filed on May 5, 2010, the whole content of which is incorporated herein by explicit reference for all intents and purposes.

FIELD OF THE INVENTION

The present invention describes methods to image amyloid beta in the retina of the eye in such a way as to diagnose, track changes and potentially treat Alzheimer's disease.

BACKGROUND OF THE INVENTION

Current methods for diagnosing Alzheimer's disease are primarily via clinical evaluation of symptoms. Proposed methods are invasive, including assessment of amyloid beta (Aβ) and other substances in the cerebral spinal fluid, the blood or genetic markers, among others. Other methods of scanning the brain are expensive and not widely available, including brain scans via MRI and PET scanning, using molecules which bind to Aβ, tagged with radionucleotide markers. The presence of Aβ in neural tissue is recognized as indicative of Alzheimer's disease. There is a need for a readily available, objective, relatively inexpensive diagnostic for Alzheimer's disease with the potential to allow longitudinal quantification of disease progression, which is sensitive and specific and would enable earlier and more accurate diagnosis. Differential detection of Aβ in the neural tissue of the retina provides such a diagnostic.

Optical imaging is advantageous because it is relatively noninvasive and without the risk of radiation exposure. In diagnosing Alzheimer's disease, optical imaging of the brain has been proposed but this is most suitable for imaging through the thinner skull of rodent models of the disease, rather than through the human skull.

It would be advantageous to provide an optical method of imaging in the eye which would provide a differential diagnosis of Alzheimer's disease. Optical imaging in the eye has the advantage of scattering much less light than the brain with an optical window through the front of the eye, transparent to wavelengths in the visible and infrared. This allows the neural tissue at the rear of the eye, the neural retina, to be imaged. There is also an ongoing need to image the induction, the progression and the results of treatment of the disease in animal models of Alzheimer's disease, including but not limited to rodent models of Alzheimer's disease.

SUMMARY OF THE INVENTION

Thus the methods described are aimed at the differential diagnosis of humans suspected of having Alzheimer's disease and potential treatment in the retina of Aβ deposits.

An embodiment provides a method for detecting and imaging amyloid beta (Aβ) or any precursor thereof of amyloid beta in the retina of the eye of a mammal for detecting Alzheimer's disease, comprising the steps of a) performing large field imaging of the retina using retinal imaging light with sufficient depth resolution to ensure detection of Aβ or any precursor thereof located close to, or on, the anterior surface of the retina which are associated with Alzheimer's disease, with the large field imaging giving full coverage of the en face portion of the retina and detecting for a marker of amyloid beta or any precursor thereof associated with Alzheimer's disease as a function of position on the retina in close proximity to, or on, the anterior surface during the large field imaging of the retina; and b) if at least one area presents the marker in a location close to, or on, the anterior surface of the retina, then magnifying and increasing the resolution of the at least one area and characterizing a size and shape of Aβ or any precursor thereof or a strength of the marker of Aβ or any precursor thereof and confirming the location close to, or on, the anterior surface and correlating the properties of Aβ or any precursor thereof to diagnose the mammal with Alzheimer's disease.

The step a) of performing large field imaging the location close to, or on, the anterior surface may include optical coherence tomography (OCT) comprising the steps of:

a) Illuminating the location close to, or on, the anterior surface using with light from a light source with sufficient bandwidth to give a retinal depth resolution of about 50 microns or less, b) focusing the light on anterior layers of the retina, c) performing an A scan to a depth of about 50 microns from the retinal surface so as to give a shorter complete scan, and d) selecting a spacing of adjacent line scans in a B scan configuration to be equal to, or smaller than, an estimated point spread function on the retina, approximately 10 microns such that full en face coverage of the retina is achieved.

The step b) of detecting for a marker of Aβ or any precursor thereof may include applying a fluorescent substance to the eye which binds to Aβ or any precursor thereof, including a) directing an ingoing retinal imaging light beam to the location close to, or on, the anterior surface to obtain an image of the location close to, or on, the anterior surface, b) directing an ingoing fluorescence excitation beam to the location close to, or on, the anterior surface with a wavelength that excites the fluorescent substance in combination with the Aβ or any precursor thereof chosen in either one or two photon excitation, c) combining the ingoing fluorescence excitation beam and the ingoing retinal imaging light beam, d) filtering an outgoing retinal imaging light beam from outgoing fluorescent light emitted by the fluorescent substance bound to any Aβ or any precursor thereof present at the location close to, or on, the anterior surface, e) detecting the outgoing fluorescent light and outgoing retinal imaging light beam and recording images of each;

f) superimposing the images of the outgoing retinal imaging light beam and images of the outgoing fluorescence light; and g) quantifying an amount of and location of fluorescence emitted by the fluorescent substance in combination with the Aβ or any precursor thereof at the location close to, or on, the anterior surface.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION OF THE INVENTION

Figure 1:
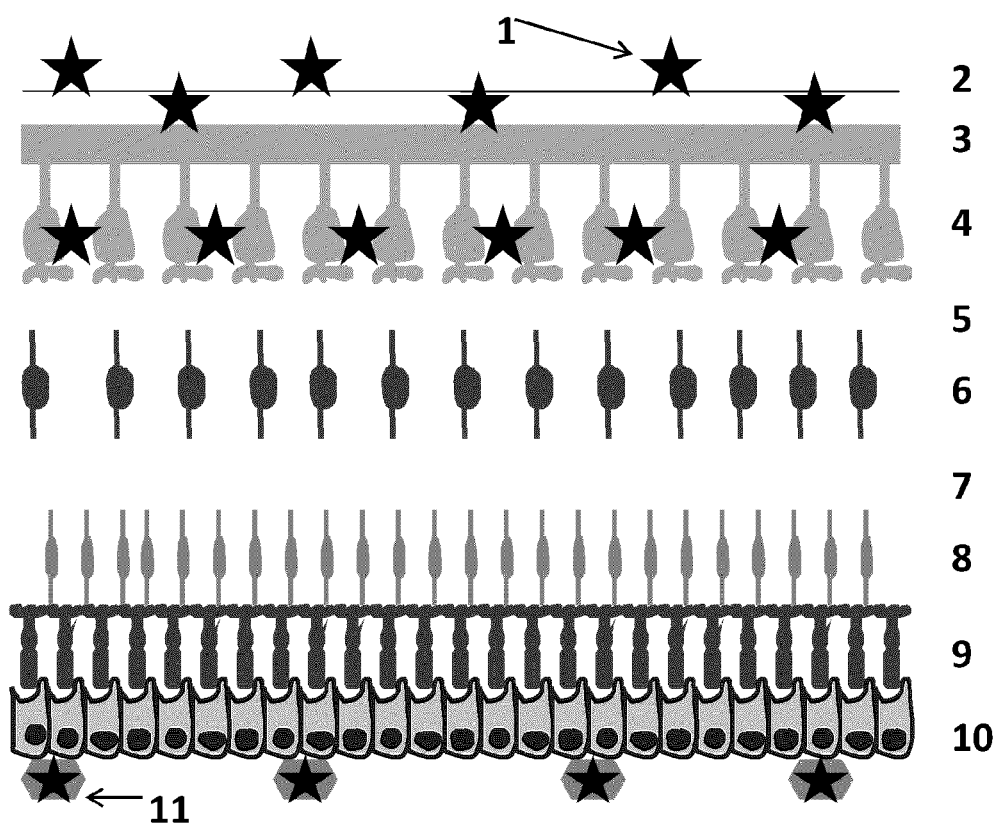
FIG. 1 is a schematic of the cell layers of the retina (2-10) which shows the positions in which Aβ, schematically shown as stars, (1) has been found in our study of postmortem retinas and studies by others of animal postmortem retinas. Drusen (11), associated with the retinal pigment epithelium (10) is found in association with the retinal disease, age related macular degeneration, not a neurodegenerative disease. The Aβ associated with Alzheimer's disease, is close to the top surface of the retina (inner limiting membrane, 2), or just below, associated with the neural cell layer of ganglion cells (4) and their nerve fibres (optic nerve fibre layer, (3). There are also Mueller cell feet which form 2 and with which the Aβ nay be associated. In animal models, sparse deposits have been found in other layers (5, 6, 7, 8, 9), sometimes in association with Alzheimer's disease.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in this specification including claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the phrase "en face" refers to the view of the retina if you are looking towards it from the direction of the crystalline lens, that is looking in the same direction as the incoming light. An observer would see the two dimensional anterior surface and if images are taken below that, other 2D layers of retinal cells.

As used herein, the phrase "large field imaging" means imaging a field normally imaged in traditional clinical imaging of the back of the eye, in this usage at least a 10 degrees by 10 degree en face image or a larger en face image or a three dimensional image where the enface dimension is at least 10 degrees by 10 degrees.

As used herein, the phrase "marker" is intended to indicate a subset of biomarkers. In the official National Institutes of Health definition, a biomarker is: "a characteristic that is objectively measured and evaluated as an indicator of normal biologic processes," or "pathogenic processes." The pathogenic process that is evaluated here is the presence of amyloid beta or any precursor thereof.

As used herein, the phrase "performing an A scan" is understood to mean that during OCT of the retina, an A-scan is an axial scan, representing reflected optical amplitude along the axis of light propagation, through the layers of the retina.

As used herein, the phrase "performing a B scan" is understood to mean that during OCT of the retina, a B-scan refers to a cross-sectional image where one axis of the image is an A scan and the amplitudes of reflections are represented in a gray scale or a false-color scale.

As used herein, the phrase "performing a C scan" is understood to mean that during OCT of the retina, a C-scan refers to a section across structures at an equal optical delay which in the retina corresponds to the coronal section, which is often modified to produce a C scan from a dataset which is a cross section parallel to the retina vitreal surface.

As used herein, the phrases "Using adaptive optics" or "applying adaptive optics correction to light focused" refers to the correction of the wavefront of light ingoing incident on the retina and the further correction of the wavefront reflected outgoing from the retina. The ingoing correction produces an image of a point on the retina which is much smaller laterally and in depth than before the wavefront correction. The lateral resolution is then improved so that objects closer together (and perpendicular to the direction of light) can be resolved. The depth resolution is also improved in some imaging methods by the correction of the ingoing wavefront or by the correction of the outgoing wavefronts in others or by the correction of both. Improved depth resolution means that two objects at a smaller separation along the direction of light propagation can be resolved.

As used herein, the phrase "small point spread function on the retina" relates to approaching the smallest point spread function on the retina which is produced by diffraction of light from a point source by the pupil. When adaptive optics correction is perfect, the smallest is approached.

As used herein, the phrase "calculating small point spread function on the retina" means that if the adaptive optics correction is not perfect, the point spread function will be larger than the smallest given when the wavefront is a sphere and can be calculated from the residual wavefront difference from a sphere which is usually given by data from the adaptive optics system.

As used herein, the phrase "estimating small point spread function on the retina" means estimating it as the smallest possible spot due to diffraction at that pupil size.

The following examples are presented to enable those skilled in the art to understand and to practice embodiments of the present disclosure. They should not be considered as a limitation on the scope of the present embodiments, but merely as being illustrative and representative thereof.

The specific embodiments described below have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Aβ has been found in the crystalline lens of the eye using a variety of techniques. In the crystalline lens of the eye, it is found in animal models of Alzheimer's disease as well as in both humans with Alzheimer's disease and normal humans. Thus it does not appear to be specific enough to allow the diagnosis of Alzheimer's disease. In addition, Alzheimer's disease is known to reduce visual function in a way that suggests damage to the neural cells of the retina of the eye. At the time of our provisional patent, Aβ had been found in the retinas of animal models of Alzheimer's disease and in the postmortem retinas of humans in association with other disorders. Prior to our work, there was a report of a single retina in which there was some weak evidence of the presence of Aβ in association with Alzheimer's disease. There had been no evidence of Aβ in living human retinas in association with Alzheimer's disease.

Aβ has been found in humans in drusen, an abnormality associated with a different disease, age related macular degeneration. These deposits are located below the neural retina. The presence of Aβ has also been suggested in the presence of glaucoma, a disease in which the neurons of the retina are damaged. A relationship between glaucoma and Alzheimer's disease has not been established.

Thus it may be important to locate the Aβ within the neural retina where it may have deleterious effects on visual function. In addition, I postulate that the type and density of Aβ in the neural retina will bear a relationship with its occurrence in the brain. Thus a method which locates Aβ in the neural retina is advantageous to the diagnosis of Alzheimer's disease, to tracking disease severity, to assessing the efficacy of treatments of Alzheimer's disease and potentially to treating the effects of Aβ deposits in the retina. These advantages apply both to humans and to animals which develop conditions similar to Alzheimer's disease in which novel diagnostics and therapies are tested.

The concept of diagnosing Alzheimer's disease through the detection of Aβ in a number of eye tissues has been previously addressed. However, prior to our provisional patent, the proposed methods were not specific enough to differentiate Aβ present due to other causes (like age related macular degeneration) from Aβ due to Alzheimer's disease (or related neurodegenerative diseases) or even to account for background fluorescence due to the retinal tissue. Others have proposed methods to image the damage to the optic nerve fibre layer due to the presence of Aβ in the disease glaucoma. Their method would not differentiate damage from Aβ from damage from other sources, including other mechanisms postulated to damage the optic nerve fibre layer in glaucoma. The patent does not make a link between the Aβ deposits or the damage from these deposits and a diagnosis of Alzheimer's disease. It would be more specific and diagnostic to image directly Aβ within or close to the neural layers of the retina.

The inventor's work on postmortem retinas of human's with a diagnosis of Alzheimer's disease (and no diagnosis of glaucoma) found and characterized, for the first time, Aβ in the neural layers of postmortem human retina in subjects with Alzheimer's disease while retinas from humans without a diagnosis of Alzheimer's disease (or dementia) were negative. We have seen fluorescence associated with Aβ which can be differentiated from the background. The deposits in the Alzheimer's retinas are in a location spatially distinct from the location of deposits associated with AMD. The deposits are located close to the nerve fibre layer and ganglion cell layer, a location expected from studies on animal models.

Subsequent to the filing of the priority US provisional application on which this application is based, a study has been published which also shows fluorescent deposits in the postmortem retinas of humans with Alzheimer's disease and in the retinas of animal models of Alzheimer's disease while showing no deposits in the retinas of humans with no diagnosis of Alzheimer's disease, (Koronyo-Hamaoui, M., et al., Identification of amyloid plaques in retinas from Alzheimer's patients and noninvasive in vivo optical imaging of retinal plaques in a mouse model, NeuroImage (2011 January; 54 Suppl 1:S204-17) The authors of this subsequent study did not discuss characterization of the deposits identified by fluorescence as to their size, shape or most importantly how their location in depth within the retina would be determined in vivo.

The present inventors have used fluorescence to initially locate the deposits. Next additional imaging techniques were used to determine whether the deposits were located within or close to the neural cell layers of the retina. Some fluorescent deposits were located deeper in the retina, consistent with AMD. However, we also localized A$\beta$ deposits to layers close to the anterior surface of the retina, the layer of ganglion neural cells and their associated nerve fibres (optic nerve fibre layer) and the inner limiting membrane, over top of theses fibres. In addition, using a high resolution imaging technique, the morphology of the deposits located close to the neural cell layers was studied by the inventors. The morphology is consistent with A$\beta$ and is distinct from the morphology of the crystalline lens fragment found on the anterior surface of one retina. The morphology of the deposits is consistent with the morphology of previously studied A$\beta$ deposits and of morphologies found in the brain in association with Alzheimer's disease. Thus it would be very useful to develop and apply high resolution imaging techniques that allow the localization within cell layers and characterization of the deposits in the living eye.

In the present application the inventors have also mapped the distributions of deposits of A$\beta$ in the postmortem retinas of humans with Alzheimer's disease or related dementias, that is, where the deposits are relative to the central area of vision. Sometimes there were many multiple deposits and sometimes there were sparsely distributed deposits. These deposits were found more often nearer the horizontal midline of the retina and closer to the central retina rather than in the far periphery. It would be useful to use these findings to design an imaging method for location such deposits.

It may be that A$\beta$ deposits associated with other neurodegenerative diseases and dementias, including glaucoma, may also be found by the methodologies proposed here. A$\beta$ has been found in animal models in association with glaucoma. This would not be surprising as glaucoma is also known to damage neural tissue in the brain as well as the retina. However, if A$\beta$ in the neural layers were located, other symptoms and changes in the eye associated with glaucoma could be assessed to rule out glaucoma before confirming a diagnosis of Alzheimer's disease.

The present patent application discloses imaging methods that can be used on the living human and animal retina in order to find, characterize and possibly treat A$\beta$ associated with Alzheimer's disease. Recently a number of new methods of imaging the retina have been developed, some of which have the resolution and coverage needed to resolve A$\beta$ deposits from surrounding structures. However, better depth resolution means that only a thin layer of the retina is imaged and imaging the full depth with that resolution is time consuming. In the same way, better lateral resolution allows resolution in that dimension but normally restricts the area of the retina that can be imaged at one time with full resolution and coverage and prolongs an imaging session that attempts to image the full retina. Thus it is a good idea to target areas of the retina in which A$\beta$ is more likely to be found in order to find what may be sparse deposits without an unreasonably long imaging session. It is also advantageous to choose and modify the imaging modality to give the needed resolution and coverage of the retina. In addition, it would be reasonable to use a marker of A$\beta$ in lower resolution imaging conditions in which A$\beta$ can be detected but not resolved into individual deposits.

The variability in the number and density of deposits gives raise to our hypothesis that the number and density may be a marker of the stage of the disease. The inventor's research has also documented differing types of A$\beta$ deposits within postmortem retinas of humans with Alzheimer's disease and based on these results it is postulated that these differing types may provide insight into subtypes of the disease and/or disease severity. They will allow staging of Alzheimer's disease via quantification and characterization of the A$\beta$.

Thioflavin-s, used in the past as a marker of A$\beta$, produces diffuse fluorescence throughout the retina and a particular signature due to thioflavin-s. However, in the simplest optical imaging using a camera (for the postmortem retina) or flood illumination and a camera for a retina imaging system in the living eye, the signal from the fluorescence would not be localized to a single depth plane. Furthermore a simple fluorescent measurement does not allow quantification of the severity of the disease or characterization of the deposits. The method proposed here will locate precisely A$\beta$ in the retina and will distinguish A$\beta$ in the retina, associated with Alzheimer's disease (or related neurodegenerative diseases) from A$\beta$ due to other causes. It will allow staging of Alzheimer's disease via quantification and characterization of the A$\beta$. The present inventors have seen fluorescence, indicative of A$\beta$ on the surface of a postmortem human retina where the structure stained is consistent with a fragment of crystalline lens. This fragment is likely present secondary to the removal of the crystalline lens and the installation of an IOL. Others have seen A$\beta$ in drusen on the anterior surface of the human retina, in association with age related macular degeneration. It is important to differentiate A$\beta$ due to these disorders (crystalline lens fragment, AMD) which are more prevalent with aging from Alzheimer's disease also prevalent with ageing.

Other fluorescent markers of A$\beta$ have been used in the postmortem retina and in locating A$\beta$ in brain tissues or have been advanced as potential markers of A$\beta$.

Besides fluorescence markers, other markers of A$\beta$ previously discussed in locations other than the retina include its interaction with polarized light either alone or in conjunction with the dye, Congo red; its interaction with light which can produce spectroscopic signatures. It is also postulated here that light may show a differential optical path and/or scattering characteristics.

Spectroscopy of blood and spinal fluid has been postulated as a potential diagnostic of Alzheimer's disease. Spectroscopy in the retina has been used in the past primarily to assess the oxygen content of the tissues or blood in the vessels, to assess lipofuscein in the aging retina and AMD and the pigments of the central retinal area. To the inventor's knowledge, it has not been postulated as a method of assessing the presence of A$\beta$ in the retina in association with Alzheimer's disease.

Eye movements have been controlled by software and hardware methods to allow a light stimulus to be placed precisely on the retina during adaptive optics correction. There is a need to use this technology in a new method to assess a marker for A$\beta$ over an extended period of time from a structure with characteristics of A$\beta$ associated with Alzheimer's disease in order to get confirmation. The steps required in the invention are firstly to image close to the surface of the retina with sufficient depth resolution to differentiate the anterior layers of the retina (including the retinal nerve fibre layer (NFL) and the ganglion cell layer (GCL) from underlying neurons from the more posterior layers, including the photoreceptor and retinal pigment epithelium (RPE) and any associated lipofuscin deposits or drusen, known to contain Aβ associate with AMD (FIG. 1). The method involves en face scanning of a relatively large area of the retina, reasonably rapidly which preferably in humans should extend 140 degrees along the horizontal, ±70 degrees nasal and temporal to the optic nerve head along the horizontal, with imaging ±20 degrees to the horizontal.

Figure 2:
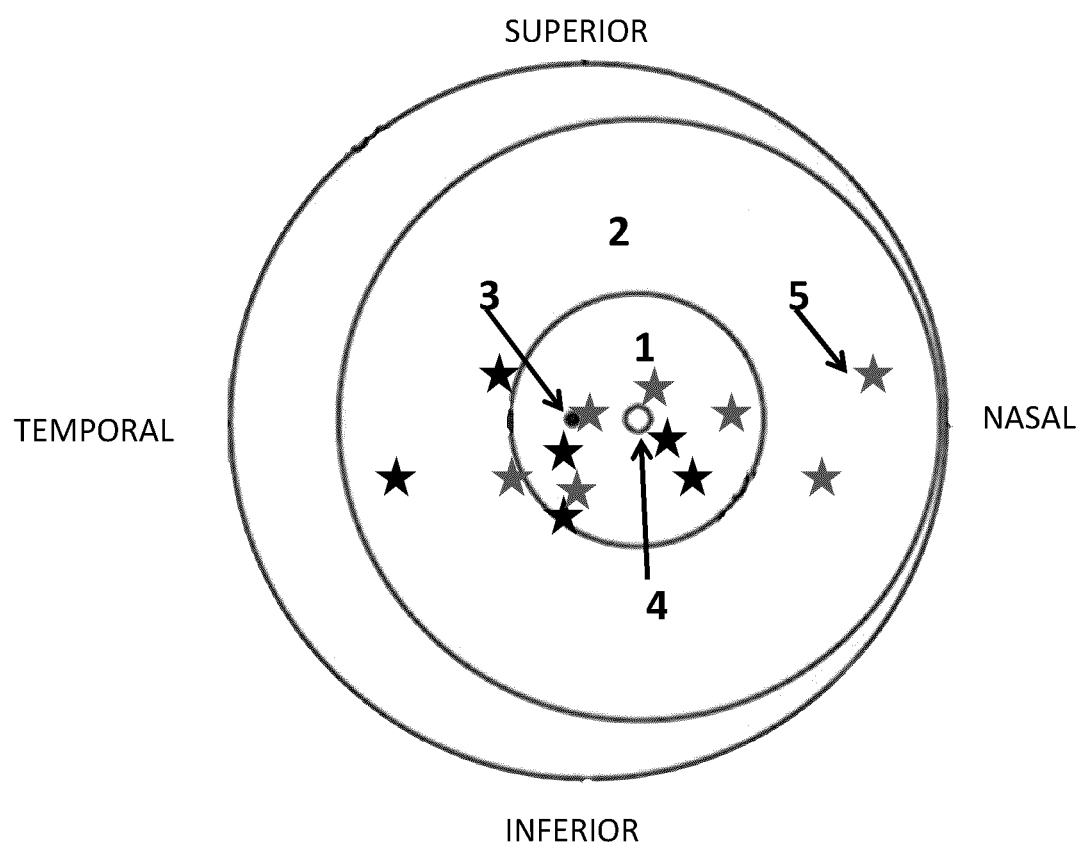
FIG. 2 shows an enface schematic view of the retina with the locations of Aβ deposits in postmortem retinas with Alzheimer's and other nonspecific dementias as found by my research group. These locations informed the design of the imaging method—as deposits were seldom found in the far periphery, were more numerous closer to the fovea and were preferentially found nearer the horizontal meridian of the retina. Schematically represented are 1, the mire central area of the retina, 2, the surface of the retina outside the central area, 3, the fovea, 4 the optic nerve head and 5, peripheral areas of the retina.

Initial studies by the inventors with respect to measurement of postmortem human retinas with Alzheimer's disease and other non specific dementias, indicate that the Aβ deposits were all found within this region. To date the majority of deposits are located within 20 degrees of the optic nerve head, but some sparse deposits are located further nasal or temporal and are sometimes the only deposit imaged in that retina. With increased experience in this imaging, the areas of the retina could be adjusted to those in which Aβ is first found during the course of Alzheimer's disease or to those to which the disease is most likely to appear first or to those to which the disease is most likely to progress over time. What is key in this first imaging step is that the imaging beam covers the full area so that no small sparse deposits are missed. Secondly the signal measured must be that coming from anterior layers (FIG. 2).

Figure 4:
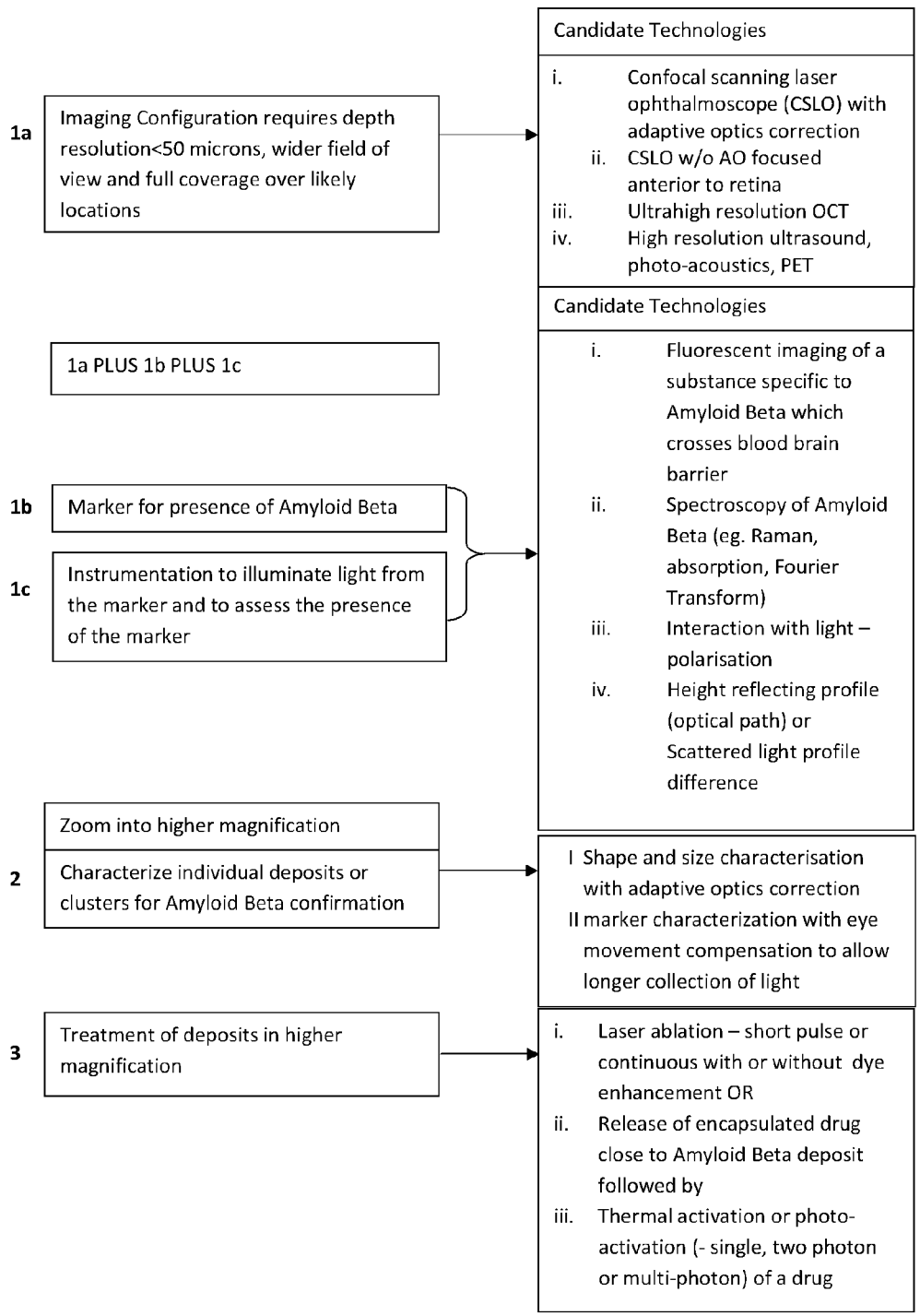
FIG. 4 shows the key steps in the method of diagnosis of Alzheimer's disease, and potential treatment of the Aβ deposits. In the first step (1) 1a, 1b, and 1c should be combined. Step 2 then proceeds followed if deemed necessary by step 3.

The steps required to image Aβ for the diagnosis of Alzheimer's disease, are summarized in FIG. 4. In the first step, sufficient depth resolution is needed to differentiate the anterior layers of the retina from the more posterior layers. Lateral resolution is not necessary at this stage, although the imaging method must sample the full en face area of the retina of interest without gaps. In this first step the light or other energy returning from the retina needs to be analyzed for a marker of Aβ in the region of the retina consistent with Alzheimer's disease. Candidate markers include fluorescent substances, spectroscopic signals, differential polarization signals, optical path difference or a difference in scattered light. These signals could be from Aβ or any of its precursor molecules. The second step is to zoom into areas which show the presence of the marker in the expected area with higher magnification and then assess the shape and size characteristics as well as strength and spatial distribution signals from markers within the previously identified areas, using an adaptive optics correction to achieve the needed lateral resolution. In the third step, light based image guided treatment of the Aβ deposits can be performed if deemed necessary.

More particularly, methods of imaging for the first step in imaging a larger area of the retina at the correct depth shown in FIG. 4 and include, but are not limited to, flood illumination of the retina incorporating optical methods to limit the depth of field (that is the thickness of the retina imaged) possibly but not limited to a stereoscopic method. Confocal scanning laser ophthalmoscopy with or without depth resolution improved through a confocal pinhole and/or adaptive optics correction can provide up to 20 microns of resolution, better than the estimated 50 microns needed. If just a confocal pinhole or a detector without pinhole were used, without adaptive optics, then an imaging plane just anterior to the surface of the inner limiting membrane should be chosen so that the poorer depth resolution would still allow the separation of imaging signals from Aβ in the anterior layers from those in posterior layers. Both flood illumination and confocal scanning laser ophthalmoscopy (CSLO) have the advantage of full coverage, with the proviso that the scanners for CSLO should ideally have a continuous movement or the steps should be no larger than the calculated size of the point spread function on the retina, either with or without adaptive optics so that light signals from sparse deposits will still be seen. In practice, given a realistic scanner resolution in an adaptive optics corrected CSLO, this implies imaging fields which are 5 degrees by 5 degrees (25 degrees square) which are scanned over the area of interest in strips moving outwards from the fovea to cover the 140 degree by 40 degree area of interest (5600 square degrees), giving 220 fields which could be imaged in a scan of approximately 8 minutes.

If the CSLO were not adaptive optics corrected, but the focus was offset anterior of the inner limiting membrane, field sizes of 10 degrees by 10 degrees would allow complete coverage of small, sparse deposits (100 square degrees), allowing a much more rapid scanning of the 5600 square degree area of interest in the same manner as described above.

Ultra high resolution optical coherence tomography (UHROCT) with a light source with sufficient bandwidth to give the needed retinal depth resolution is also a candidate for the initial larger field imaging and would be focused on the anterior layers of the retina. Again it is important that full en face coverage of the retina be achieved. Continuous scanners give full coverage. In choosing the spacing of adjacent line scans in the usual B scan configuration, the line spacing should be about 10 microns so as approximately match the point spread on the retina. The depth of the scan needed is only about 50 microns from the retinal surface so the A scan depth should be limited to give faster scanning. Again, given usual digital resolutions, if the UHROCT is not AO corrected for the initial larger field scan, the scan should be about 10 degrees by 10 degrees. However, this scan will take much longer than the time for the CSLO scan above given the need for an A scan.

A combination in the first step of the faster non adaptive optics corrected CSLO scan to identify a marker of Aβ followed by the UHROCT scan described for the areas in which the marker is evident is advantageous. The restricted areas and depth of UHROCT scans will save time but the better UHROCT depth resolution will confirm that the marker is coming from Aβ in the layer associated with Alzheimer's disease.

Two photon fluorescence imaging of a marker of Aβ would have the required depth resolution of the anterior retinal layers. Imaging of an intrinsic fluorescent marker would require too many frames and time to get resolution and sufficient signal over a large area. If an extrinsic fluorescent marker with a large cross section and brightness and without toxicity were available for Aβ, this imaging would be feasible. The preference would be for a marker excited in the infrared. Then the delivery light could potentially be the same in the CSLO wide field imaging channel and the two photon excitation channel, simplifying instrument design.

The required depth resolution is likely less than 50 microns. Other imaging techniques such as ultra high resolution ultrasound, photo-acoustics or PET would also be possible if the needed depth resolution of the living retina could be demonstrated.

The method of imaging the larger area of the retina is combined with a marker of the presence of Aβ (FIG. 4). Thus the retina can be imaged at lower resolutions, which may be used to speed up the coverage of the complete retina. A first possible marker includes fluorescent molecules which are non toxic to humans which include, but are not limited to, smart optical probes that emit characteristic fluorescence signals only when bound to Aβ, and other fluorescent dyes such as the near-infrared fluorescence oxazine dye AOI987, curcumin-derivatized CRANAD-2, thioflavin T or thioflavin S or one of their derivatives or Congo red. If fluorescence were used, the method of imaging the larger area of the retina would then include a wavelength that would excite the molecule chosen in either one or two photon excitation, and a filter system to separate the incident and fluorescent light and a detector sensitive to the fluorescent light. The detector filter and detector are chosen to emphasize the wavelength of fluorescence of the marker in combination with Aβ in order to deemphasize the background tissue fluorescence.

Among the possible fluorescence markers that can be used are those which can cross the blood brain barrier. This allows intravenous administration in this method. However, other methods of delivery of the fluorescence markers, including intravitreal injection are also possible as the structures to be stained are close to the anterior retinal surface. Methods of delivery used to stain the crystalline lens could also be used to deliver stain to the anterior retina with potentially improved specificity over staining the lens alone.

Figure 3:
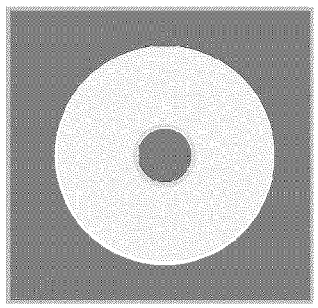
FIG. 3 shows the shapes of fluorescent deposits found in postmortem retinas with Alzheimer's disease. This includes donut shapes (1), fibrillar shapes (2) and globular shapes (3). The size and shape of these shapes is important to differentiating the presence of Aβ due to Alzheimer's disease from stray crystalline lens fibres, one of which was found by the inventors, sitting on the surface of the postmortem retina. This fibre presumably was left behind subsequent to the removal of the crystalline lens during known cataract surgery. The inventors contemplate that the sizes and shapes of these deposits in combination with their quantity and location can be used to diagnose the stage and subtype of Alzheimer's disease.
Figure 3:
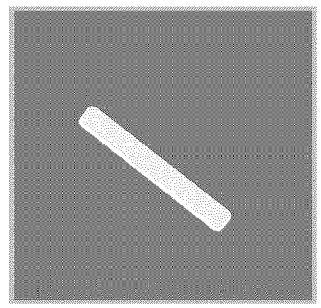
Figure 3:
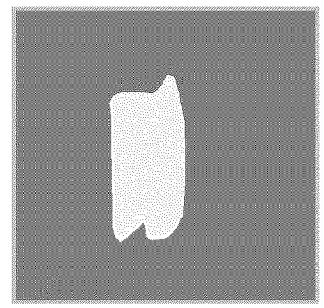

Light can be used to release the fluorescent dye of choice which can be delivered in liposomal capsules. The release of this dye may be localized by light to retinal vessels near the surface of the retina in the areas of the retina in which one is examining for A. In the case of one photon or two photon excitation of the fluorescence, the excitation beam may be focused at, or slightly anterior to, the retinal surface, in order to excite Aβ deposits closer to the anterior surface of the retina and reduce the fluorescent light returning from deeper deposits not associated with Alzheimer's disease. Fluorescence as described in the foregoing can also be used to specify the structure and shape (FIG. 3) of the Aβ deposit (FIG. 4—step 2). In the same way that Aβ can be marked with fluorescent dyes, other dyes may be used to mark precursors of Aβ or smaller subunits of Aβ. These are expected to occur in similar regions to those in which we have observed Aβ deposits.

A second possible marker of Aβ deposits (Step 1b FIG. 4) is spectroscopy. This includes but is not limited to Raman spectroscopy, absorption spectroscopy, fluorescence correlation spectroscopy, NMR spectroscopy, quasi-elastic light-scattering spectroscopy, circular dichroism spectroscopy and Fourier transform spectroscopy of Aβ deposits measured for the first time in the expected layers of the retina. The beam used for the spectroscopy could be, but is not limited to the same beam as used to image in CSLO or UHROCT. Even if not the same beam, the spectroscopic beam should be focused close to the anterior layer of the retina. The spectroscopic signal interrogated must be one that is not absorbed either by the water in the eye or by pigments in the elderly crystalline lens and should be returning from the retina, more specifically from a layer of the retina within 50 microns of the retina vitreal interface. The spectroscopic signal could be generated by the Aβ deposits alone or by the Aβ deposits in combination with a dye for example but not limited to Congo red. Spectroscopy as described in the foregoing can also be used to specify the structure and shape (FIG. 3) of the Aβ deposits (FIG. 4—step 2). In the same way that Aβ can be marked and detected via spectroscopy, spectroscopy may also be used to mark precursors of Aβ or smaller subunits of Aβ. These are expected to occur in similar regions to those in which we have observed Aβ deposits.

As a third possible marker, polarization imaging (Step 1b FIG. 4) could be used with CSLO or UHROCT imaging or combined with any of the other marker techniques mentioned above and the fourth marker (light scattering) described below. The Aβ deposits would then be visible via differential absorption, scattering or reflection of polarized light (ie optical activity), or by polarization spectroscopy or by differential reflection of polarised light from the Aβ deposits in comparison with the retina without Aβ deposits. It is expected that the deposits themselves will be optically active due to their fibrillar nature. In addition an optically active dye such as but not restricted to Congo red may be used. This may include characterizing one or more of the Jones matrix or Mueller matrix components across the retina or performing a polarization imaging method known to enhance the contrast of structures with differing polarization properties (e.g., confocal scanning laser ophthalmoscopy improved using Mueller matrix polarimetry) or detecting structures because they have differing effects on a polarization property of the light. Depth resolved polarization OCT could also be used. Polarization imaging as described in the foregoing could also be used to characterize the deposits and to specify the structure and shape (FIG. 3) of the deposit (FIG. 4—step 2).

A fourth possible marker (Step 1b FIG. 4) is the light scattering characteristics and differing intrinsic properties of the Aβ deposit including the following. For deposits close to the anterior limiting membrane, the Aβ deposits may be visible without fluorescence as a depth deformation of the retinal surface, visible in any of the techniques mentioned above or as an area of differing optical path length, visible with optical coherence tomography or in confocal scanning laser ophthalmoscopy with the use of an indirect aperture. The height difference that it is important to resolve from the other retinal layers is one to several microns (often less than 10 microns). Thus the depth resolution required for any of the imaging modalities mentioned above has to be excellent if intrinsic Aβ properties are to be imaged as markers. For instance the OCT spectrum would need to be much broader than that needed to determine that a fluorescence signal from the OCT signal originates in the anterior 50 microns of the retina. The UHR OCT scan should include the retinal vitreal interface in order to assess the presence of deformation or optical path differences due to Aβ deposits close to the surface. The scan of the OCT would need to be denser in order to specify the structure and shape (FIG. 3) of the deposit (FIG. 4—step 2).

In order for a confocal scanning laser ophthalmoscopy to detect the deformation of the retinal surface by an Aβ deposit, the CSLO would need to be adaptive optics corrected and perhaps illuminated with a two photon source to further improve depth resolution. In order for a CSLO to detect light scattered from the retinal vitreal surface, an indirect confocal aperture could be used while focusing the instrument anterior to the retinal vitreal interface.

Other optical techniques may be used to assess whether the surface of the inner limiting membrane has been deformed by an Aβ deposit. Some of these assess the specular nature of the reflection from the inner limiting membrane and may be used to assess changes in normal age matched subjects and those with Aβ deposits secondary to Alzheimer's disease. Other methods which measure the size of particles between approximately one and a few microns via scattered light may also be used as the presence of each deposit or cluster of deposits should create differential scattered light. These methods include the polarization methods described above. Any of the light scattering characteristics or differing intrinsic optical properties of an Aβ deposit or assessment of the deformation of the inner limiting membrane described in the foregoing could be used in order to specify the structure and shape (FIG. 3) of an Aβ deposit (FIG. 4—step 2).

In step 1, (FIG. 4), a map of the Aβ deposits across the retina (or the subregion considered) and their density would then be generated for longitudinal comparison and comparison with data collected from postmortem retinas and animal models. As the method is used, population data of the variation of the structure and density of Aβ deposits and their locations in the retina (in depth with respect to the inner limiting membrane and on retinal location with respect to the fovea) with disease stage, (measured using independent methods) will be generated. Also considered will be the intensity of light associated with the chosen marker(s). This will lead in turn to metrics of Alzheimer's disease diagnosis and of disease severity and subtype, leading to monitoring of progression of the disease and the utility of any treatment in humans and in animal models of the disease.

If the markers described above are specific and sensitive to Alzheimer's disease and the number and/or position and/or density of deposits in step 1 is sensitive to Alzheimer's disease progression, step 2 (FIG. 4) may not be necessary to a diagnostic instrument. However the results could then be contaminated by the presence of lens fragments which are known to be positive for Aβ and are expected close to the retina surface in those who have had cataract surgery.

Once the locations and densities of the deposits have been determined, individual deposits in each region of the retina where they occur will be characterized (step2, FIG. 4). This will potentially assist in staging the disease and in determining variants of the disease. This will likely not be time consuming because visible deposits are expected to be sparse or clustered together (as found postmortem). This will require a higher resolution (and smaller field of view) imaging method. The deposits will be differentiated from lens fragments at this stage, sized and likely categorized into amorphous deposits, donut-like deposits, fibrillar-like deposits and possibly plague like deposits, all consistent with Alzheimer's disease and the strength and high resolution of marker(s) may be measured. In addition, higher resolution will allow the size of the deposits (lateral extent and height) to be specified.

Deposits from other sources (including those with dimensions consistent with fragments from the crystalline lens) will not result in a diagnosis of Alzheimer's disease. It is expected that later stage disease will be associated both with larger deposits and deposits that are either more fibrillar or plague like. In combining all the steps into one instrument, a zoom system which allows the change from large to small field of view or a lower lateral resolution instrument with an aligned higher resolution instrument will be necessary. To achieve the required high resolution to image the small deposits in animal models and human eyes will likely require an adaptive optics corrected instrument (including but not limited to an adaptive optics corrected CSLO or OCT or combination with sufficient wavefront correction and pixel resolution to resolve and categorize deposits of a lateral dimensions from a few microns up to about 10 microns (donut deposits) up to 20 microns for fibrillar deposits and 40 microns and larger for amorphous deposits, as found by the inventor's group in postmortem retinas.

In specifying the progression of the disease and variants of Alzheimer's disease, markers discussed previously may be used in combination. In that case, the most sensitive marker will be used to locate Aβ deposits with additional markers being assessed only in the regions where Aβ deposits have been located.

It is possible that there will not be sufficient light back from an Aβ specific marker in step1 (or when multiple markers are assessed to allow a definitive categorization as an Aβ deposit or to categorize the disease. If this is the case, a software or hardware module to control eye movements will be used in conjunction with one of the markers discussed above in step 1b (FIG. 4). Methods of compensating for eye movements include real time software compensation and hardware compensation. They are able to control eye movements to within a few microns. This would allow light that may contain information for a positive marker for Aβ to be collected from a single region of the retina, of a size expected for an Aβ deposit, for an extended period of time, giving a higher signal and allowing the region to be confirmed or not as being Aβ consistent with Alzheimer's disease or a subtype.

The imaging of Aβ deposits consistent with Alzheimer's disease will also facilitate their treatment. This treatment could use the same all or a subset of the CSLO channel with a smaller field of view, an adaptive optics correction and eye movement compensation to allow a laser beam to be used to ablate sparse deposits without affecting the adjacent tissue. A potentially pre-corrected and pre-shaped laser beam would be focused on or slightly anterior to the Aβ deposit, allowing it to be ablated. In addition, dye which binds to Aβ could be pre-delivered to the deposit (possibly for diagnostic purposes) and a laser light beam can be used which is absorbed by the dye. This dye could be the fluorescent dye where the light delivered for ablation is of higher local retinal irradiance than the light used to excite fluorescence. The laser energy could be continuous or a short brief pulse.

Other light activated treatments of the Aβ deposits will also be enabled by the methods described. The mechanism may be directly on the deposit by light (as previously described) or on an agent delivered to the Aβ deposits by any means including but not limited to intravenous injection and intravitreal injection. The agent with the therapeutic effect may be enclosed and the light may affect the enclosure in order to release the therapeutic agent close to the deposit (and the neurons in close proximity to and potentially adversely affected by Aβ deposit). The mechanism of action of the light energy is intended to be general by single photon, or by two-photon or by multiphoton absorption resulting in any mechanism of damage. This includes but is not limited to thermal mechanisms or other direct light treatment of the deposit, photoactivation of drugs, photoactivation of molecules that then release drugs, release of drugs from enclosures (from within a molecule or larger enclosure) via light energy, among others.

The methods disclosed herein may be extended to map the Aβ deposits in locations known to be associated with glaucoma. Differentiation between glaucoma and Alzheimer's disease could be through imaging of the deposits and their sizes, shapes, density, location and interaction with any of the markers discussed. If none of these characteristics differ between Aβ deposits present in glaucoma and in Alzheimer's disease, the diagnosis of a neurodegenerative disease affecting the retina will be made. Other symptoms associated with the two conditions will then lead to a differential diagnosis. It is possible that other neurodegenerative diseases may lead to Aβ deposits which could be characterized by the methods described. The characteristics of the Aβ deposits may differ among these conditions or other symptoms may need to be assessed to differentiate among neurodegenerative conditions.

The methods described are specifically designed to differentiate between Aβ deposits found in conjunction with Alzheimer's disease (and other neurodegenerative diseases) and Aβ deposits present in drusen as a marker for the severity of age related macular degeneration AMD. However, if the position of focus of the light used is changed from the anterior portion of the retina to the posterior portion, close to the RPE and drusen, the foregoing methods could be generalized to diagnose and assess the progression of AMD.

Preferred Implementation

Figure 5:
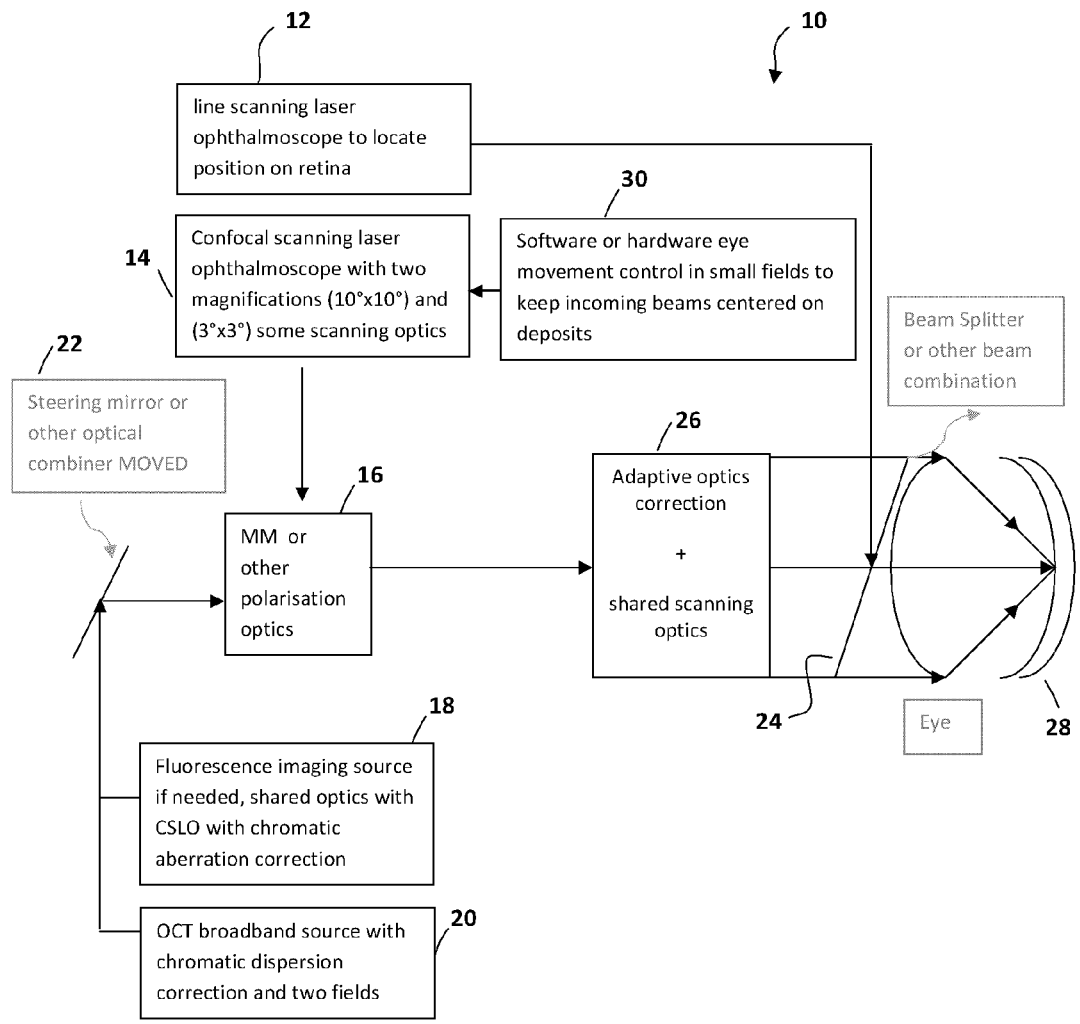
FIG. 5 gives the preferred implementation of the ingoing light to accomplish steps 1, 2 and 3 from FIG. 4. The boxes on the left share optics as much as possible and if they have differing light sources, the beams are recombined in alignment on entering the eye. Light sources may be shared between fluorescence imaging and the CSLO source or between fluorescence imaging and the OCT source. The OCT and/or CSLO sources may be chosen to allow spectroscopy or analysis of other optical signals following reflection. Any of the different sources may be sent through the polarization optics or any may bypass the polarization optics and enter the beam path post polarization optics. The adaptive optics correction will be shared and as far as possible some of the scanning optics will be shared among channels. In this configuration the beam will be corrected with adaptive optics on the ingoing path. However, in the wider field of view, this correction will mimic a flat mirror or be replaced by a flat mirror flipped into the system. In the smaller field of view, a software or hardware channel compensates for eye movements to keep the imaging detectors centered on the potential Aβ structures while the markers of Aβ are assessed for longer periods if necessary.
Figure 6:
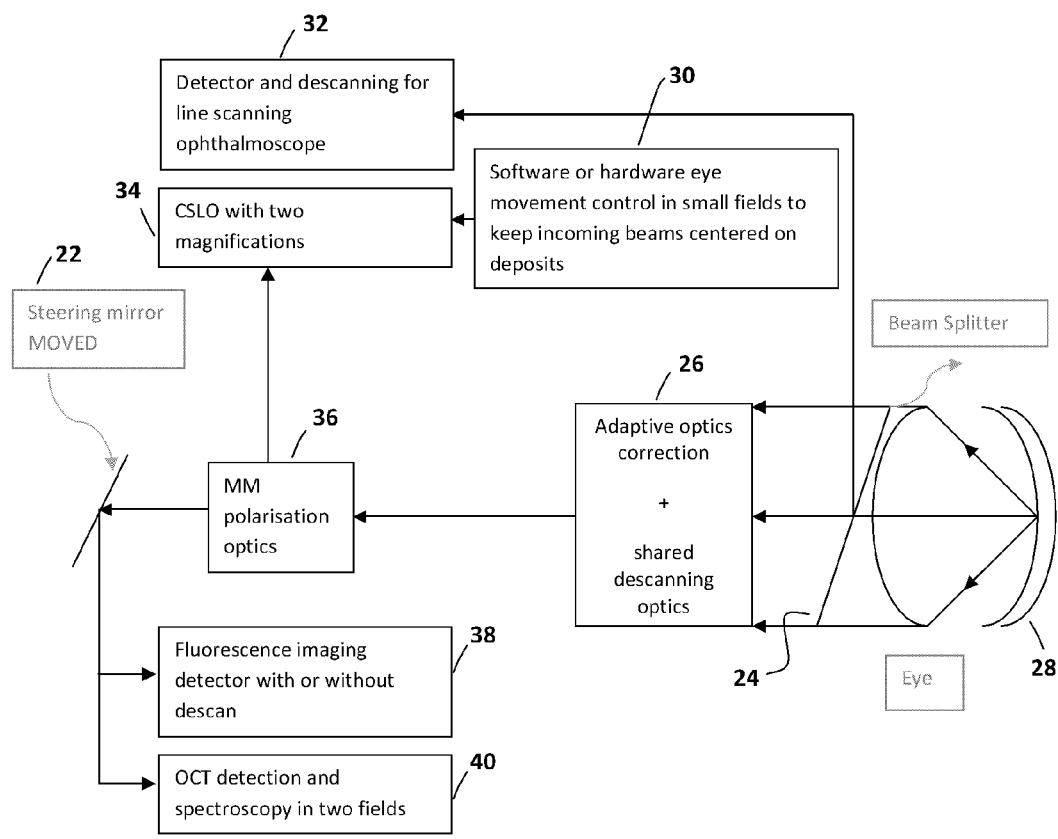
FIG. 6 gives the preferred implementation for the beam paths of the light leaving the eye and reentering the instrument. In this configuration, the beam will be recorrected with adaptive optics on the reverse path. However, in the wider field of view, this correction will mimic a flat mirror or be replaced by a flat mirror flipped into the system. As far as possible, the descanning and other optics will be shared. In this implementation, the polarization of all beams is assessed on the outgoing path—this can be modified in other implementations to direct the beam to any of the modules prior to the polarization assessment. Fluorescence detection can be done before or after descan. OCT detection includes spectroscopy in this implementation. In other implementations spectroscopy could be implemented in the CSLO channel or the fluorescence channel. In the smaller field of view, a software or hardware channel compensates for eye movements to keep the imaging detectors centered on the potential Aβ structures while the markers of Aβ are assessed for longer periods of time if necessary.

For step 1, one preferred implementation is a low lateral resolution line scanning confocal laser ophthalmoscope with a broader line FIGS. 5 and 6), used in a one photon fluorescence imaging mode. Although this will have a lower lateral resolution than other instruments, it will guarantee that all of the retina of interest is illuminated in a few fields and sparse, small retinal deposits are not missed. Alternately a full confocal scanning laser ophthalmoscope will be used with a confocal pinhole to improve depth resolution. The line scan confocal module is then used to give a reference view of the retina with the current fields of the other modules overlaid (FIGS. 5 and 6, 12, 32). The CSLO wavelength in the preferred implementation is infrared.

Referring to FIG. 5, a novel aspect of the instrument (16) is the choice of fields of view, retinal area scanned, depth and lateral resolutions, the fluorescence optics and other aspects of design to maximize the ability to detect sparse deposits of Aβ and characterize their properties in a two step process. The portion of the apparatus for directing the beam(s) of light into the patient's eye includes (12) a low resolution module for imaging the full retina, with the location of the fields of the other modules indicated on it. The lower resolution field (10 by 10 degrees) of the confocal scanning laser ophthalmoscope (14) provides the low resolution image discussed in step1 of FIG. 4 by a scan of the 10 degree by 10 degree field over the larger retinal area of interest. This module has two novel aspects: 1) when the retinal vitreal interface has been focused and a scan of the retina is desired, the module automatically defocuses slightly anterior to the retina vitreal interface thereby giving detection of those Aβ deposits located in the anterior retina and 2) the scanning beam of the module gives full coverage of the retina such that single small Aβ deposits are always covered by the imaging beam.

A fluorescence imaging source (18) shares scanning optics (26 and other scans), field sizes and position of focus with the CSLO so as to share the full coverage of the retina and may share the incident beam. This CSLO module is unique as the fluorescence excitation wavelength, optics (including incident and emission filters) will be chosen to detect Aβ deposits or their precursors.

An OCT module with a source broad enough to give less than 50 microns resolution (20) is used in its larger field of view with correction for the chromatic dispersion of the eye to indicate whether Aβ deposits are located within 50 microns of the anterior surface of the retina. It shares some scanning optics with the CSLO (26) such that the location of the CSLO and OCT scans are on the same region of retina at any time. If the OCT module is implemented in the small field of view to provide additional Aβ markers, then a UHR-OCT with a broader source is needed to give the resolution to characterize the dimensions of Aβ deposits (approximately 3 microns in depth).

The steering mirror (22) in the position shown sends all beams (12, 14, 18, 20) into (16) such that the polarization of the ingoing light is controlled and potentially varied. 22 may be moved or duplicated so that some beams are not polarized. When the field of view of 14 is changed to a lower size (3 degrees by 3 degrees, higher resolution and higher magnification) (step 2 FIG. 4), the adaptive optics correction in 26 is turned on to pre-correct the wavefront of the eye and this correction is also applied to 18 and 20 which also then use smaller, magnified fields of view.

In step 2, if the signal from a marker is low, software or hardware eye movement control (30) is activated. 30 is also activated during image guided treatment. The beam combiner (24) combines all beams entering the eye where the eye's optics in combination with any needed optical correction, focuses light onto the anterior surface of the retina (28).

Referring to FIG. 6, the portion of the apparatus for receiving the light reflected from the patient's eye includes an optical device for example a beam splitter (24) which allows some light (of the wavelength of the corresponding source) to be sent directly to optics and descanning optics and a detector for a larger field imager (32). The rest of the light goes through common scanning optics and an adaptive optics correction (26) which is only active in the magnified, small field view. Light at some or all other wavelengths then enters polarization optics (36) if desired, and then via steering mirror(s) (22) the detection channel for the CSLO input wavelength (34) with descanning optics, and the fluorescence imaging detector for the emission wavelength (38). Prior to this detector there may be descanning optics (which may be shared with the CSLO, 34) or the detector area may be larger without descan.

Light corresponding to the incident wavelength of the OCT is sent to the OCT detection system (40) which includes, in this implementation, a module which records a spectroscopic signature of Aβ deposits or their precursors.

In use, preferred implementation is to use the confocal scanning laser ophthalmoscope with a fluorescence imaging channel and an initial large field of 10 by 10 degrees (14, 34). The fluorescence imaging mode (18, 38) is used with a fluorescence dye which has a high specificity for Aβ, has a high photon yield and is excited in the infrared where more light can be placed into the eye. The preferred implementation is to use a dye (which can cross the blood neural retina barrier) which is administered intravenously in a lipid formulation that allows localized light excitation in the retina. If the dye is excited in the infrared, then the confocal scanning laser ophthalmoscope can be changed from a non-fluorescent (34) to a fluorescent mode by directing light from an IR detector to a detector sensitive to the fluorescent emission wavelength (38). There will also be a chromatic aberration correction in the fluorescence detection channel. If the overall instrument has an adaptive optics module in a smaller field of view (26) (FIGS. 5 and 6), then the fluorescent excitation will be localized in depth to retinal layers close to the anterior retinal surface (where the instrument is focused) and a confocal pinhole in front of the fluorescence detector is not used in this implementation. To get full retinal coverage, a preferred implementation is to use the fluorescence imaging (18,38) in a large field of view with the adaptive optics mirror (26) set to a flat reference. When a fluorescing structure is imaged, the smaller field and the adaptive optics module is activated. If the fluorescent structure remains sharply focused, it is located in the anterior layers of the retina, consistent with Aβ found as a marker of Alzheimer's disease.

This is the instrument module (18, 38) with 14, 34 that will be used to initially in a larger field of view to locate the Aβ and create a retinal map of density and location. In the preferred implementation, this instrument will share an adaptive optics channel (26) (to increase depth resolution in the small field of view) with the rest of the instrument. The instrument would have an adjustable focus so that images could be taken near the anterior of the retina, it will have a scanning mode that allows the 10 deg by 10 deg field to be scanned over a retinal area up to 140 degrees by 40 degrees and it will have the capability of averaging a large number of frames to increase if necessary, the sensitivity to the fluorescence.

In order for the instrument to be used to distinguish subtypes of Alzheimer's disease and the stage of the disease, the CSLO module has a smaller field of view (larger magnification 3 degrees by 3 degrees) (14, 34) which will allow a magnified, high resolution view of the Aβ deposits to allow them to be characterized, both with (18,38) and without fluorescence and with the adaptive optics correction active (26). An eye motion tracking module (30) is included in this preferred implementation which allows the imaging to be performed on a similar small field for a prolonged period of time in order to improve the signal to noise.

An additional instrument module consists of a UHR optical coherence tomography module (20, 40) which shares the slower line scan and the adaptive optics module with the CSLO. This module has a 5 degree by 5 degree enface scan combined with a rapid A (depth) scan. This A scan will be performed with restricted depth to concentrate on the anterior retina and to reduce the elapsed time of the scan. The light source for the UHROCT in this implementation is a broad infrared source allowing 3 microns of depth resolution. This source is separated from the CSLO source so that optics and scanners can be shared but the beams can be sent to separate detectors. This allows the high resolution CSLO and UHROCT images of individual deposits to be acquired simultaneously and overlaid for increased information. It is expected that additional markers of Aβ deposits may be needed for their precise characterization. In this preferred implementation, Mueller matrix (MM) polarimetry modules on the ingoing (16) and outgoing arms (36) can be used in conjunction with the fluorescence module, the CSLO and/or the UHROCT modules, both to improve the image contrast of the Aβ deposits and to characterize their interaction with polarization states of light. The UHROCT and CSLO with MM polarimetry will be used to characterize the size, morphology and type of Aβ deposits.

The UHROCT (20, 40) with an adaptive optics (26) and dispersion corrections will in this implementation, give additional 3 D information as to the depth of the Aβ deposits and their depth profiles across a high resolution en face view. That will allow the instrument to distinguish between amorphous deposits and donut-like deposits. In this preferred implementation, an OCT detection module capable of IR spectroscopy (20, 40) is included to allow additional characterization of the deposits and any precursor molecules nearby.

The preferred implementation of a therapeutic instrument is to use as a treatment beam the infrared CSLO beam (14) at a higher energy than the imaging modality. The treatment would be focused at the layer of the Aβ deposits with adaptive optics correction (26) to localize the energy laterally and in depth. The CSLO scan will be programmed to deliver higher energy only in the regions of Aβ deposits. The energy would be preferentially absorbed because of the presence of the fluorescent dye, excited at this wavelength. The Aβ deposits would be ablated by this method.

The steps required to achieve high depth and lateral resolution in all the modules of the instrument include firstly the correction of the first order chromatic aberration of the eye. This can be accomplished in a number of ways with the preferred implementation being the use of an achromatizing lens to introduce the opposite chromatic aberration to that within the target eye for the wavelengths incident on the eye. This would ideally include amounts of transverse and longitudinal chromatic aberration opposite to those of the eye. The preferred wavelength range used has a midpoint in the infrared. In addition higher order dispersion correction may improve the resolution of the UHROCT (20, 40) module. The second step is correction of the second order and higher aberrations of the optics of the eye. The first order aberrations may also be corrected. This is accomplished by the use of an adaptive optics element (26) to pre-distort the wavefront entering the eye. This device may also pre-tilt the wavefront. The pre-distortion and pre-tilting are such that the wavefront incident on the point of interest on the retina is a sphere centered at that point. In the preferred implementation, this pre-distortion (and pre-tilt if used) is accomplished by measuring the wavefront in a feedback loop with a wavefront measuring device. The preferred implementation is a closed loop system (26). This methodology works for both animal eyes for the testing of localized light therapies and on humans for light based therapy, tracking of the effects of therapy and imaging the eye. In order to quickly reach the anterior layer of interest in the fundus, particularly in animal models, the wavefront shaping device should be one with a large amount of stroke. The preferred implementation is to use a magnetic mirror which has the required amount of stroke but any other wavefront shaping device or combinations of devices with similar effective strokes are possible. It is also a preferred implementation to enter through a pupil that allows the light to enter the full pupil available which may be defined (in infrared light) not by the natural or drug dilated pupil but by the aperture of the crystalline lens of the eye. The use of specific wavelengths of light may mean that the light can penetrate the iris giving a larger effective aperture size.

It will be understood that in the event Aβ or any precursor thereof is detected, it may be characterized to differentiate among Aβ associated with Alzheimer's disease and Aβ associated with other neurodegenerative diseases including glaucoma, leading to a differential diagnosis of these diseases.

In addition where plane of focus at or near the anterior surface of the retina is replaced with plane of focus at or near the RPE where the Aβ may be detected, it may be characterized and associated with age related macular degeneration (AMD) leading to a diagnosis of AMD.

Thus to summarize, the invention provides a method for detecting and imaging amyloid beta (Aβ) or any precursor thereof of amyloid beta in the retina of the eye of a mammal for detecting Alzheimer's disease, comprising the steps of a) performing large field imaging of the retina using retinal imaging light with sufficient depth resolution to ensure detection of Aβ or any precursor thereof located close to, or on, the anterior surface of the retina which are associated with Alzheimer's disease, with the large field imaging giving full coverage of the en face portion of the retina and detecting for a marker of amyloid beta or any precursor thereof associated with Alzheimer's disease as a function of position on the retina in close proximity to, or on, the anterior surface during the large field imaging of the retina; and b) if at least one area presents the marker in a location close to, or on, the anterior surface of the retina, then magnifying and increasing the resolution of the at least one area and characterizing a size and shape of Aβ or any precursor thereof or a strength of the marker of Aβ or any precursor thereof and confirming the location close to, or on, the anterior surface and correlating the properties of Aβ or any precursor thereof to diagnose the mammal with Alzheimer's disease.

When detected, the method includes correlating any one or combination of size, shape, location, numbers and density and strength of marker(s) of the Aβ or any precursor thereof to diagnose Alzheimer's disease.

When detected, the method includes using the result of correlating the size, shape, location, numbers and density and strength of marker(s) of the Aβ or any precursor thereof to diagnose Alzheimer's disease to determine a stage of the Alzheimer's disease.

In addition, the method may include using the result of correlating the size, shape, location, numbers and density and strength of marker(s) of the Aβ or any precursor thereof to diagnose Alzheimer's disease to determine a subtype of the disease.

The method may include using a longitudinal change in any combination of the sizes, shapes, locations, numbers and densities and strength of marker(s) of the Aβ or any precursor thereof to determine the progression of Alzheimer's disease between two or more time points.

The step a) of performing large field imaging may include obtaining one or more images from humans extending approximately 140 degrees along a horizontal, which is ±70 degrees nasal and temporal to the human's optic nerve head along the horizontal, with imaging of 40 degrees in the vertical which is ±20 degrees to the horizontal.

The step a) of performing large field imaging may include flood illumination of the retina including limiting a depth of field of the retina being imaged.

The step a) of performing large field imaging may include obtaining the image of the location close to, or on, the anterior surface using scanning laser ophthalmoscopy (SLO) with a detector of limited area such that the depth of field is limited by the detector area, comprising the steps of
 a) imaging the location close to, or on, the anterior surface at a plane just anterior to the surface of the inner limiting membrane such that a depth resolution allows separation of imaging signals from the Aβ or any precursor thereof in anterior layers from those in posterior layers of the retina; and
 b) scanning continuously or in steps which are no larger than a calculated size of a point spread function on the retina such that there are no gaps in the en face area of the retina scanned and imaged so that light from sparse deposits is observable.

The step a) of performing large field imaging may include scanning the location close to, or on, the anterior surface using a confocal scanning laser ophthalmoscopy comprising the steps of
 a) imaging the location close to, or on, the anterior surface through a confocal pinhole configured to give a depth resolution of about 50 microns or less; and
 b) scanning the location close to, or on, the anterior surface continuously or in steps which are no larger than a estimated size of a point spread function on the retina such that there are no gaps in the en face area of the retina scanned and imaged so that light from sparse deposits is observable. In this regard scanning the location close to, or on, the anterior surface is conducted in steps, and using adaptive optics to give a depth resolution of 50 microns or less, and including
 a) calculating the small point spread function on the retina, or assume 3 microns and
 b) scanning the location close to, or on, the anterior surface in steps small enough such that there are no gaps in the en face area of the retina scanned and imaged so that light from sparse deposits is observable.

The step a) of performing large field imaging may include using optical coherence tomography (OCT) comprising the steps of:
 a) Illuminating the location close to, or on, the anterior surface using with light from a light source with sufficient bandwidth to give a retinal depth resolution of about 50 microns or less,
 b) focusing the light on anterior layers of the retina,
 c) performing an A scan to a depth of about 50 microns from the retinal surface so as to give a shorter complete scan, and
 d) selecting a spacing of adjacent line scans in a B scan configuration to be equal to, or smaller than, an estimated point spread function on the retina, approximately 10 microns such that full en face coverage of the retina is achieved. In this regard the optical coherence tomography may be conducted using any one or combination of an A scan configuration, a B scan configuration, and a C scan configuration, to obtain full en face coverage of the retina with depth resolution equal to or less than about 50 microns. Further, in this regard the method may include applying adaptive optics correction to light focused on the anterior layers of the retina and when using the B scan choosing a spacing of adjacent line scans in a B scan configuration to be equal to or smaller than the estimated point spread function on the retina, approximately 3 microns to obtain full en face coverage of the retina with a resulting larger number of steps per unit distance on the retina.

The step a) of performing large field imaging may include obtaining full coverage by scanning a smaller field of view with full coverage over an area of interest at a rate that allows a number of images to be acquired at each position before moving the field of view to an adjacent position, with a current field of view position overlapping with all adjacent field of view positions and as the field of view is moved, a position of focus is adjusted to keep the focus close to the surface of the retina.

The step a) of performing large field imaging may include obtaining full coverage given by scanning a smaller field of view with full coverage over an area of interest at a continuous rate that allows more than a dozen frames to be acquired at each position and as the field being imaged moves, a position of focus is adjusted to keep the focus close to the surface of the retina.

The step a) of performing large field imaging may include optically imaging with a depth resolution of 50 microns or less and full coverage of the en face retina over a desired area.

The step a) of performing large field imaging may include using positron emission tomography (PET) imaging of the location close to, or on, the anterior surface of the retina. The positron emission tomography may be obtained using a positron emission tomography apparatus configured to have a depth resolution of 50 microns or less and full coverage of the en face retina over a desired area.

The step b) of detecting for a marker of Aβ or any precursor thereof may include applying a fluorescent substance to the eye which binds to Aβ or any precursor thereof, including
 a) directing an ingoing retinal imaging light beam to the location close to, or on, the anterior surface to obtain an image of the location close to, or on, the anterior surface,
 b) directing an ingoing fluorescence excitation beam to the location close to, or on, the anterior surface with a wavelength that excites the fluorescent substance in combination with the Aβ or any precursor thereof chosen in either one or two photon excitation,
 c) combining the ingoing fluorescence excitation beam and the ingoing retinal imaging light beam,
 d) filtering an outgoing retinal imaging light beam from outgoing fluorescent light emitted by the fluorescent substance bound to any Aβ or any precursor thereof present at the location close to, or on, the anterior surface,
 e) detecting the outgoing fluorescent light and outgoing retinal imaging light beam and recording images of each;
 f) superimposing the images of the outgoing retinal imaging light beam and images of the outgoing fluorescence light; and
 g) quantifying an amount of and location of fluorescence emitted by the fluorescent substance in combination with the Aβ or any precursor thereof at the location close to, or on, the anterior surface. In this regard, a the method may use a fluorescent excitation light source, filter and detectors for detecting the outgoing fluorescent light and fluorescent substance which are configured to emphasize an amount of fluorescence emitted by the fluorescent substance in combination with Aβ and to deemphasize any background tissue fluorescence. In this regard the fluorescent substance may be a fluorescent molecule selected from the group consisting of oxazine dye AOI987, curcumin-derivatized substances, thioflavin T, thioflavin S, Congo red, any combination therefore, and any physiologically compatible derivatives thereof. In this regard the fluorescent substance may be optical probe molecules that emit characteristic fluorescence signals only when bound to Aβ or any precursor thereof. The fluorescent substance may be nanoparticles that emit characteristic fluorescence signals only when bound to Aβ or any precursor thereof. The fluorescent substance may be selected such that it can cross the blood brain barrier, and wherein the fluorescent substance is delivered to the eye via intravenous administration either as a pure fluorescent substance or in combination with a carrier. The fluorescent substance may be delivered by intravitreal injection either as a pure marker or in combination with a carrier. The fluorescent substance may be delivered to a posterior chamber of the eye by any means and diffuses to the retina. The fluorescent substance may be delivered to the tear film and diffuses through the cornea, the anterior chamber and posterior chamber of the eye to the retina. The fluorescent substance may be delivered to the anterior chamber of the eye and diffuses through the anterior chamber and the posterior chamber of the eye to the retina. The fluorescent substance may be excited by infrared light, and wherein the fluorescence excitation light and retinal imaging light is the same wavelength. The step a) of performing large field imaging may include fluorescence imaging of a marker of Aβ or any precursor thereof, using two photon excitation of intrinsic fluorescence of Aβ near the anterior surface of the retina such that this imaging gives a required depth resolution of the anterior retinal layers.

The marker may include a spectroscopic emission signal emitted by Aβ alone or Aβ in combination with a dye or any precursor thereof alone or any precursor thereof in combination with a dye, said spectroscopic emission signal being any one or combination of Raman spectroscopy signals, absorption spectroscopy signals, fluorescence correlation spectroscopy signals, NMR spectroscopy signals, quasi-elastic light-scattering spectroscopy signals, circular dichroism spectroscopy signals or Fourier transform spectroscopy signals, and wherein an ingoing beam of light producing the spectroscopic emission signals is focused close to, or on, the anterior layer of the retina, and wherein the ingoing beam has wavelength selected so that the beam passes through the anterior structures of the eye without absorption.

In this regard the ingoing beam of light which produces the spectroscopic emission signals may be different from the retinal imaging light and has a bandwidth limited to that which will produce a spectroscopic signature of Aβ or any precursor thereof. Or, in the alternative, the ingoing beam of light used to produce the spectroscopic emission may be the same as the retinal imaging light. The spectroscopic emission signals measured may be localized to the anterior surface of the retina or an area close to the anterior surface of the retina by use of confocal scanning laser ophthalmoscopy combined with a detector of the spectroscopic emission signals. The spectroscopic emission signals measured may be localized to the anterior surface of the retina or an area close to the anterior surface of the retina by the use of optical coherence tomography combined with a detector of the spectroscopic signature.

The step of detecting for the marker of Aβ or any precursor thereof may include detecting a marker which is a result of interaction of the Aβ or any precursor thereof with a polarization state of the retinal imaging light delivered to the retina and Aβ deposits or any precursor thereof are detected by any one of differential absorption, scattering and reflection of polarized light arising from optical activity of Aβ deposits or any precursor thereof. In this regard one or more component or combination of components of a polarization matrix including Jones matrix or Mueller matrix may be defined for each pixel in the image taken in claim 1 across the retina to differentiate Aβ deposits or any precursor thereof from the surrounding tissue. A polarization imaging method known to enhance the contrast of structures with differing polarization properties may be used to detect Aβ deposits or any precursor thereof. A polarization imaging method known as confocal scanning laser ophthalmoscopy improved using Mueller matrix polarimetry may be used to detect Aβ deposits or any precursor thereof. Or, a polarization imaging method known as depth resolved polarization OCT may be used to detect Aβ deposits or any precursor thereof.

The method may include using a fluorescent substance which binds to Aβ or any precursor thereof wherein the step b) of detecting for the marker of Aβ or any precursor thereof includes detecting a marker which is a result of interaction of a combination of the fluorescent substance which binds to Aβ or bound to any precursor thereof with the polarization state of light.

The marker of Aβ deposits or any precursor thereof may include light scattered from Aβ deposits or any precursor deposit thereof at or near the retinal surface and an optical method is used to detect said scattered light. In this regard the marker of Aβ or any precursor thereof is the light scattered from the retina vitreal interface which results in a detectable reduction in the brightness of the specular reflection from this surface. The scattered light may be detected by a confocal scanning laser ophthalmoscopy with the use of an indirect aperture and adaptive optics.

The marker of Aβ or any precursor thereof may be a deformation of the retinal surface of between about 1 to 10 microns, imaged by ultra high resolution optical coherence tomography giving a 3D image of the retina close to its anterior surface, The marker of Aβ or any precursor thereof may be a difference in optical path length in a local region of the retina, close to the anterior surface of the retina, visible with ultra high resolution optical coherence tomography.

The marker of Aβ or any precursor may be a difference in optical path length in a local region of the retina, close to the anterior surface of the retina, visible with confocal scanning laser ophthalmoscopy with adaptive optics.

As used herein, the terms "comprises", "comprising", "including" and "includes" are to be construed as being inclusive and open-ended. Specifically, when used in this document, the terms "comprises", "comprising", "including", "includes" and variations thereof, mean the specified features, steps or components are included in the described invention. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A method for detecting and imaging amyloid beta (Aβ) or any precursor thereof in the retina of the eye of a mammal for detecting Alzheimer's disease, comprising the steps of
   a) using an imaging system to perform large field imaging of the retina using retinal imaging light with sufficient depth resolution to ensure detection of Aβ or any precursor thereof located close to, or on, the anterior surface of the retina which are associated with Alzheimer's disease, with the large field imaging giving full coverage of the en face portion of the retina and detecting for a marker of amyloid beta or any precursor thereof associated with Alzheimer's disease as a function of position on the retina in close proximity to, or on, the anterior surface during the large field imaging of the retina; and b) if at least one area presents the marker of amyloid beta or any precursor thereof in a location close to, or on, the anterior surface of the retina, then magnifying and increasing the resolution of the at least one area and characterizing a size and shape of Aβ or any precursor thereof or a strength of the marker of Aβ or any precursor thereof and confirming the location close to, or on, the anterior surface and correlating the size and shape or strength of Aβ or any precursor thereof to diagnose the mammal with Alzheimer's disease.

2. The method according to claim 1 including correlating any one or combination of size, shape, location, numbers and density and strength of marker(s) of the Aβ or any precursor thereof to diagnose Alzheimer's disease.

3. The method according to claim 2 including using the result of correlating the size, shape, location, numbers and density and strength of marker(s) of the Aβ or any precursor thereof to diagnose Alzheimer's disease to determine a stage of the Alzheimer's disease.

4. The method according to claim 2 including using the result of correlating the size, shape, location, numbers and density and strength of marker(s) of the Aβ or any precursor thereof to diagnose Alzheimer's disease to determine a subtype of the disease.

5. The method according to claim 1 including using longitudinal change in any combination of the sizes, shapes, locations, numbers and densities and strength of marker(s) of the Aβ or any precursor thereof to determine the progression of Alzheimer's disease between two or more time points.

6. The method according to claim 1 wherein said step a) of performing large field imaging includes obtaining one or more images from humans extending approximately 140 degrees along a horizontal, which is ±70 degrees nasal and temporal to the human's optic nerve head along the horizontal, with imaging of 40 degrees in the vertical which is ±20 degrees to the horizontal.

7. The method according to claim 1 wherein said step a) of performing large field imaging includes flood illumination of the retina including limiting a depth of field of the retina being imaged.

8. The method according to claim 1 wherein said step a) of performing large field imaging includes obtaining the image of the location close to, or on, the anterior surface using scanning laser ophthalmoscopy (SLO) with a detector of limited area such that the depth of field is limited by the detector area, comprising the steps of
  imaging the location close to, or on, the anterior surface at a plane just anterior to the surface of the inner limiting membrane such that a depth resolution allows separation of imaging signals from the Aβ or any precursor thereof in anterior layers from those in posterior layers of the retina; and
  scanning continuously or in steps which are no larger than a calculated size of a point spread function on the retina such that there are no gaps in the en face area of the retina scanned and imaged so that light from sparse deposits is observable.

9. The method according to claim 1 wherein said step a) of performing large field imaging includes scanning the location close to, or on, the anterior surface using a confocal scanning laser ophthalmoscopy comprising the steps of
  a) imaging the location close to, or on, the anterior surface through a confocal pinhole configured to give a depth resolution of about 50 microns or less; and
  b) scanning the location close to, or on, the anterior surface continuously or in steps which are no larger than a estimated size of a point spread function on the retina such that there are no gaps in the en face area of the retina scanned and imaged so that light from sparse deposits is observable.

10. The method according to claim 9 wherein scanning the location close to, or on, the anterior surface is conducted in steps, and using adaptive optics to give a depth resolution of 50 microns or less, and including
  a) calculating the small point spread function on the retina, or assume 3 microns and
  b) scanning the location close to, or on, the anterior surface in steps small enough such that there are no gaps in the en face area of the retina scanned and imaged so that light from sparse deposits is observable.

11. The method according to claim 1 wherein said step a) of performing large field imaging of the location close to, or on, the anterior surface includes optical coherence tomography (OCT) comprising the steps of:
  illuminating the location close to, or on, the anterior surface using light from a light source with sufficient bandwidth to give a retinal depth resolution of about 50 microns or less,
  focusing the light on anterior layers of the retina,
  performing an A scan to a depth of about 50 microns from the retinal surface so as to give a shorter complete scan, and
  selecting a spacing of adjacent line scans in a B scan configuration to be equal to, or smaller than, an estimated point spread function on the retina of, approximately 10 microns such that full en face coverage of the retina is achieved.

12. The method according to claim 11 wherein said optical coherence tomography is conducted using any one or combination of an A scan configuration, a B scan configuration, and a C scan configuration, to obtain full en face coverage of the retina with depth resolution equal to or less than about 50 microns.

13. The method according to claim 11 including applying adaptive optics correction to light focused on the anterior layers of the retina and when using the B scan choosing a spacing of adjacent line scans in a B scan configuration to be equal to or smaller than the estimated point spread function on the retina of, approximately 3 microns to obtain full en face coverage of the retina with a resulting larger number of steps per unit distance on the retina.

14. The method according to claim 1 wherein said step a) of performing large field imaging of the location close to, or on, the anterior surface includes obtaining full coverage by scanning a smaller field of view with full coverage over an area of interest at a rate that allows a number of images to be acquired at each position before moving the field of view to an adjacent position, with a current field of view position overlapping with all adjacent field of view positions and as the field of view is moved, a position of focus is adjusted to keep the focus close to the surface of the retina.

15. The method according to claim 1 wherein said step a) of performing large field imaging of the location close to, or on, the anterior surface includes obtaining full coverage given by scanning a smaller field of view with full coverage over an area of interest at a continuous rate that allows frames to be acquired at each position and as the field being imaged moves, a position of focus is adjusted to keep the focus close to the surface of the retina.

16. The method according to claim 1 wherein said step a) of performing large field imaging of the location close to, or on, the anterior surface includes optically imaging with a depth resolution of 50 microns or less and full coverage of the en face retina over a desired area.

17. The method according to claim 1 wherein said step a) of performing large field imaging of the location close to, or on, the anterior surface includes using positron emission tomography (PET) imaging of the location close to, or on, the anterior surface of the retina.

18. The method according to claim 17 wherein said positron emission tomography is obtained using a positron emission tomography apparatus configured to have a depth resolution of 50 microns or less and full coverage of the en face retina over a desired area.

19. The method according to claim 1 wherein said step of detecting for a marker of Aβ or any precursor thereof includes applying a fluorescent substance to the eye which binds to Aβ or any precursor thereof, including
- directing an ingoing retinal imaging light beam to the location close to, or on, the anterior surface to obtain an image of the location close to, or on, the anterior surface,
- directing an ingoing fluorescence excitation beam to the location close to, or on, the anterior surface with a wavelength that excites the fluorescent substance in combination with the Aβ or any precursor thereof chosen in either one or two photon excitation,
- combining the ingoing fluorescence excitation beam and the ingoing retinal imaging light beam,
- filtering an outgoing retinal imaging light beam from outgoing fluorescent light emitted by the fluorescent substance bound to any Aβ or any precursor thereof present at the location close to, or on, the anterior surface,
- detecting the outgoing fluorescent light and outgoing retinal imaging light beam and recording images of each;
- superimposing the images of the outgoing retinal imaging light beam and images of the outgoing fluorescence light; and
- quantifying an amount of and location of fluorescence emitted by the fluorescent substance in combination with the Aβ or any precursor thereof at the location close to, or on, the anterior surface.

20. The method according to claim 19 in which a fluorescent excitation light source, filter and detectors for detecting the outgoing fluorescent light and fluorescent substance are configured to emphasize an amount of fluorescence emitted by the fluorescent substance in combination with Aβ and to deemphasize any background tissue fluorescence.

21. The method according to claim 19 wherein said fluorescent substance is a fluorescent molecule selected from the group consisting of oxazine dye AO1987, curcumin-derivatized substances, thioflavin T, thioflavin S, Congo red, any combination therefore, and any physiologically compatible derivatives thereof.

22. The method according to claim 19 wherein said fluorescent substance is optical probe molecules that emit characteristic fluorescence signals only when bound to Aβ or any precursor thereof.

23. The method according to claim 19 wherein said fluorescent substance is nanoparticles that emit characteristic fluorescence signals only when bound to Aβ or any precursor thereof.

24. The method according to claim 19 wherein said fluorescent substance is selected such that it can cross the blood brain barrier, and wherein the fluorescent substance is delivered to the eye via intravenous administration either as a pure fluorescent substance or in combination with a carrier.

25. The method according to claim 19 wherein said fluorescent substance is delivered by intravitreal injection either as a pure marker or in combination with a carrier.

26. The method according to claim 19 wherein said fluorescent substance is delivered to a posterior chamber of the eye by any means and diffuses to the retina.

27. The method according to claim 19 wherein said fluorescent substance is delivered to the tear film and diffuses through the cornea, the anterior chamber and posterior chamber of the eye to the retina.

28. The method according to claim 19 wherein said fluorescent substance is delivered to the anterior chamber of the eye and diffuses through the anterior chamber and the posterior chamber of the eye to the retina.

29. The method according to claim 19 wherein said fluorescent substance is excited by infrared light, and wherein the fluorescence excitation light and retinal imaging light is the same wavelength.

30. The method according to claim 19 wherein said step a) of performing large field imaging includes fluorescence imaging of a marker of Aβ or any precursor thereof, using two photon excitation of intrinsic fluorescence of Aβ near the anterior surface of the retina such that this imaging gives a required depth resolution of the anterior retinal layers.

31. The method according to claim 1 wherein said marker includes a spectroscopic emission signal emitted by Aβ alone or Aβ in combination with a dye or any precursor thereof alone or any precursor thereof in combination with a dye, said spectroscopic emission signal being any one or combination of Raman spectroscopy signals, absorption spectroscopy signals, fluorescence correlation spectroscopy signals, NMR spectroscopy signals, quasi-elastic light-scattering spectroscopy signals, circular dichroism spectroscopy signals or Fourier transform spectroscopy signals, and wherein an ingoing beam of light producing the spectroscopic emission signals is focused close to, or on, the anterior layer of the retina, and wherein the ingoing beam has wavelength selected so that the beam passes through the anterior structures of the eye without absorption.

32. The method according to claim 31 where the ingoing beam of light which produces the spectroscopic emission signals is different from the retinal imaging light and has a bandwidth limited to that which will produce a spectroscopic signature of Aβ or any precursor thereof.

33. The method according to claim 31 where the ingoing beam of light used to produce the spectroscopic emission is the same as the retinal imaging light.

34. The method according to claim 31 where the spectroscopic emission signals measured are localized to the anterior surface of the retina or an area close to the anterior surface of the retina by use of confocal scanning laser ophthalmoscopy combined with a detector of the spectroscopic emission signals.

35. The method according to claim 31 where the spectroscopic emission signals measured are localized to the anterior surface of the retina or an area close to the anterior surface of the retina by the use of optical coherence tomography combined with a detector of the spectroscopic signature.

36. The method according to claim 31, said method including detecting for a marker which is a result of the interaction of the Aβ or any precursor thereof with a polarization state of the retinal imaging light delivered to the retina and Aβ deposits or any precursor thereof detected by any one of differential absorption, scattering and reflection of polarized light arising from optical activity of Aβ deposits or any precursor thereof.

37. The method according to claim 1 wherein said step of detecting for the marker of Aβ or any precursor thereof includes detecting a marker which is a result of interaction of the Aβ or any precursor thereof with a polarization state of the retinal imaging light delivered to the retina and Aβ deposits or any precursor thereof are detected by any one of differential absorption, scattering and reflection of polarized light arising from optical activity of Aβ deposits or any precursor thereof.

38. The method according to claim 37 whereby one or more component or combination of components of a polarization matrix including Jones matrix or Mueller matrix is defined for each pixel in the image taken in claim 1 across the retina to differentiate Aβ deposits or any precursor thereof from the surrounding tissue.

39. The method according to claim 37 where a polarization imaging method known to enhance the contrast of structures with differing polarization properties is used to detect Aβ deposits or any precursor thereof.

40. The method according to claim 37 where a polarization imaging method known as confocal scanning laser ophthalmoscopy improved using Mueller matrix polarimetry is used to detect Aβ deposits or any precursor thereof.

41. The method according to claim 37 where a polarization imaging method known as depth resolved polarization OCT is used to detect Aβ deposits or any precursor thereof.

42. The method of claim 37 wherein the method includes the use of a fluorescent substance which binds to Aβ or any precursor thereof wherein said step of detecting for the marker of Aβ or any precursor thereof includes detecting a marker which is a result of interaction of a combination of the fluorescent substance which binds to Aβ or bound to any precursor thereof with the polarization state of light.

43. The method according to claim 37 where a polarization property is measured and the degree of fibrillar structure is deduced.

44. The method of claim 1 wherein the marker of Aβ or any precursor thereof includes light scattered from Aβ or any precursor thereof at or near the retinal surface and an optical method is used to detect said scattered light.

45. The method of claim 44 wherein the marker of Aβ or any precursor thereof is the light scattered from the retina vitreal interface which results in a detectable reduction in the brightness of the specular reflection from this surface.

46. The method of claim 44 wherein the scattered light is detected by a confocal scanning laser ophthalmoscopy with the use of an indirect aperture and adaptive optics.

47. The method of claim 1 wherein the marker of Aβ or any precursor thereof is a deformation of the retinal surface of between about 1 to 10 microns, imaged by ultra high resolution optical coherence tomography giving a 3D image of the retina close to its anterior surface.

48. The method of claim 1 wherein the marker of Aβ or any precursor thereof is a difference in optical path length in a local region of the retina, close to the anterior surface of the retina, visible with ultra high resolution optical coherence tomography.

49. The method of claim 1 wherein the marker of Aβ or any precursor is a difference in optical path length in a local region of the retina, close to the anterior surface of the retina, visible with confocal scanning laser ophthalmoscopy with adaptive optics.

50. The method according to claim 1 wherein if in step b) at least one area presents the marker in a location of the retina then the step of magnifying and increasing the resolution of the at least one area includes using a zoom system which allows a change from large field to small field of view with higher resolution within the same imaging system, said imaging system including an adaptive optics module which provides no correction to optical quality in step a) but is turned on to correct optical quality and improve resolution in step b) in order to confirm the location of the Aβ or any precursors thereof close to or on the anterior surface and to characterize its size and shape.

51. The method according to claim 50 wherein the imaging system is a confocal scanning laser ophthalmoscope.

52. The method according to claim 50 wherein the imaging system is an ultra high resolution optical coherence tomographer.

53. The method according to claim 1 wherein if in step b) at least one area presents the marker in a location of the retina, and wherein the step of magnifying and increasing the resolution of the at least one area includes using a zoom system which allows a change from large field to small field of view with higher resolution within the same imaging system wherein imaging system is an ultra high resolution optical coherence tomographer.

54. The method according to claim 1 wherein if in step b) at least one area presents the marker in a location of the retina, the step of characterizing the strength and properties of the marker of Aβ or any precursor thereof is assisted by an eye motion tracking module such that the marker is accessed within the same small field for a prolonged period of time in order to improve the signal to noise of the signal from the marker.

55. The method according to claim 1 where if Aβ or any precursor thereof is detected including characterizing it to differentiate among Aβ associated with Alzheimer's disease and Aβ associated with other neurodegenerative diseases.

56. The method according to claim 1 where plane of focus at or near the anterior surface of the retina is replaced with plane of focus at or near the retinal pigment epithelium (RPE) where the Aβ which is detected and characterized would be associated with age related macular degeneration (AMD) leading to a diagnosis of AMD.

* * * * *